(12) United States Patent
Amir et al.

(10) Patent No.: US 10,002,806 B2
(45) Date of Patent: Jun. 19, 2018

(54) METROLOGY TARGETS WITH FILLING ELEMENTS THAT REDUCE INACCURACIES AND MAINTAIN CONTRAST

(71) Applicant: KLA-Tencor Corporation, Milpitas, CA (US)

(72) Inventors: Nuriel Amir, Yokne'am (IL); Raviv Yohanan, Qiryat Motzkin (IL)

(73) Assignee: KLA-Tencor Corporation, Milpitas, CA (US)

( * ) Notice: Subject to any disclaimer, the term of this patent is extended or adjusted under 35 U.S.C. 154(b) by 4 days.

(21) Appl. No.: 14/605,425

(22) Filed: Jan. 26, 2015

(65) Prior Publication Data
US 2015/0227675 A1 Aug. 13, 2015

Related U.S. Application Data

(63) Continuation of application No. PCT/US2014/054811, filed on Sep. 9, 2014.

(60) Provisional application No. 61/939,129, filed on Feb. 12, 2014.

(51) Int. Cl.
| | |
|---|---|
| G06F 17/50 | (2006.01) |
| H01L 21/66 | (2006.01) |
| G01N 21/47 | (2006.01) |

(52) U.S. Cl.
CPC .......... *H01L 22/30* (2013.01); *G01N 21/4785* (2013.01)

(58) Field of Classification Search
USPC ............................ 716/50, 51, 52, 53, 54, 55
See application file for complete search history.

(56) References Cited

U.S. PATENT DOCUMENTS

| | | | |
|---|---|---|---|
| 6,239,031 B1 | 5/2001 | Kepler et al. | |
| 6,850,858 B1 * | 2/2005 | West | ......................... G03F 1/84 |
| | | | 257/5 |
| 2003/0223630 A1 * | 12/2003 | Adel | ...................... G03F 7/705 |
| | | | 382/145 |

(Continued)

FOREIGN PATENT DOCUMENTS

| | | |
|---|---|---|
| KR | 10-0871801 B1 | 12/2008 |
| KR | 2010-0079145 A | 7/2010 |
| KR | 2012-0025765 A | 3/2012 |

*Primary Examiner* — Brian Ngo
(74) *Attorney, Agent, or Firm* — Suiter Swantz pc llo (57) ABSTRACT

The subject application relates to metrology targets with filling elements that reduce inaccuracies and maintain contrast. The present invention provides a metrology target and a method to design the metrology target. The metrology target comprises specified filling elements introduced into identified continuous regions in a given target design, wherein parameters of the introduced filling elements are determined by a trade-off between a contrast requirement and an inaccuracy requirement which is associated via production with the identified continuous regions. The method includes the steps of identifying continuous regions in a target design, and introducing specified filling elements into the identified continuous regions, wherein parameters of the introduced filling elements are determined by a trade-off between a contrast requirement and an inaccuracy requirement which is associated via production with the identifying continuous regions. At least one of the identifying and the introducing can be carried out by at least one computer processor.

22 Claims, 9 Drawing Sheets

(56) References Cited

U.S. PATENT DOCUMENTS

2013/0330904 A1    12/2013   Yao et al.
2014/0374375 A1*   12/2014   Zwiers ............. G01N 21/95607
                                                                                    216/13

\* cited by examiner

METROLOGY TARGETS WITH FILLING
ELEMENTS THAT REDUCE INACCURACIES
AND MAINTAIN CONTRAST

CROSS-REFERENCE TO RELATED
APPLICATION

This application is filed under 35 U.S.C. § 111(a) and § 365(c) as a continuation of PCT international Patent Application No. PCT/US2014/054811, filed Sep. 9, 2014 which application claims the benefit of U.S. Provisional Patent Application No. 61/939,129 filed Feb. 12, 2014, which applications are incorporated herein by reference in their entireties.

TECHNICAL FIELD

The present invention relates to the field of metrology targets, and more particularly, to metrology targets designed to reduce specific types of inaccuracies.

BACKGROUND OF THE INVENTION

Metrology targets are used to verify the accuracy of production steps and are designed to be optically measureable. Common types of metrology targets provide optical contrast between target elements and their background regions.

The inventors have found that the common practice of separating target elements by empty background regions results in different kinds of metrology errors. The inventors have further discovered that these metrology errors may be at least partly overcome by different and advantageous target designs and design principles which are presented below. It is noted that while the disclosed ideas are mainly exemplified for segmented target elements which are separated by empty background regions, they are likewise implementable to any large featureless region such as originally unsegmented target elements, and regions in different layers of the wafer. As the terms "empty" and "segmented" depend on the respective scale, it is further noted that the dimensions which are mentioned below may be adjusted according to specific characteristics of layer and target design and of production processes, and adapted to any design and production technologies.

Figure 1A:
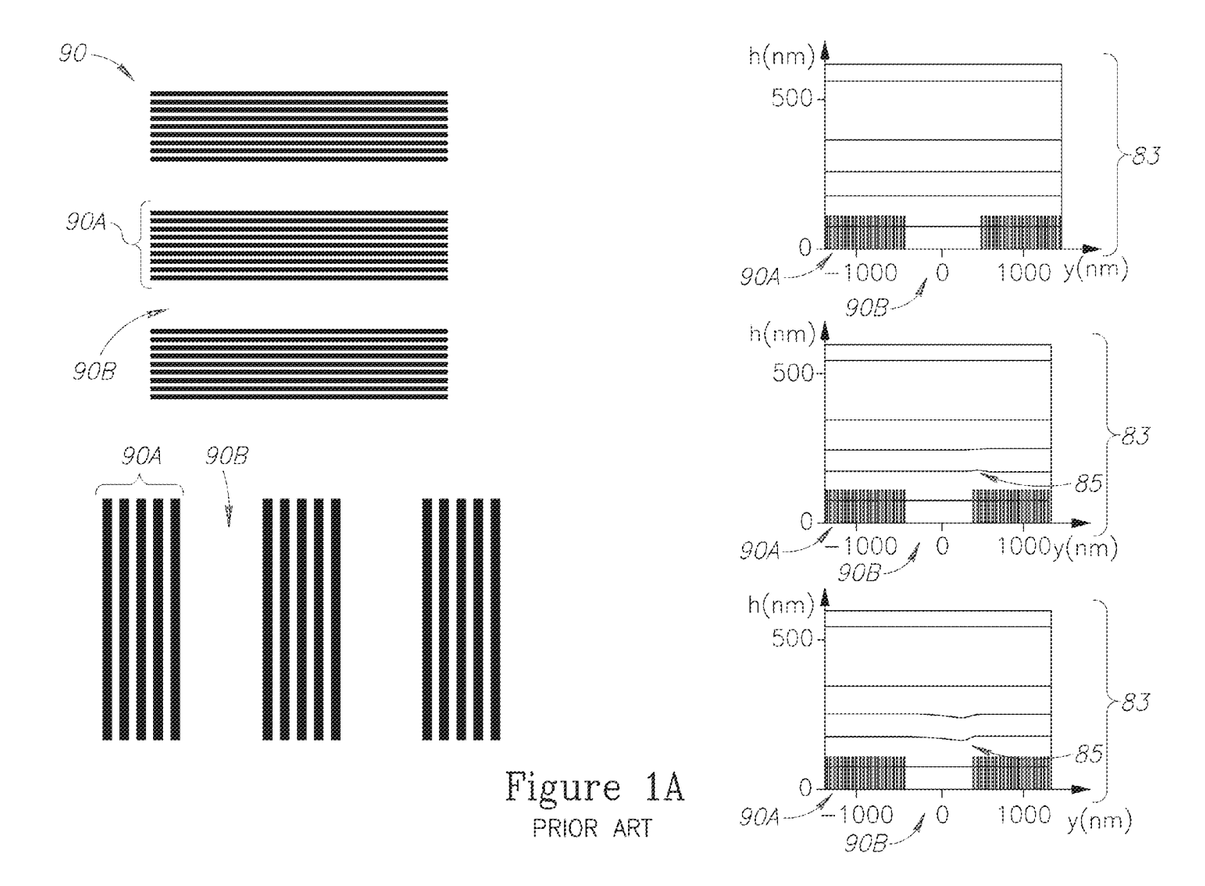
FIG. 1A illustrates a dishing effect resulting from the prior art practice of leaving empty background regions between target elements.
Figure 1B:
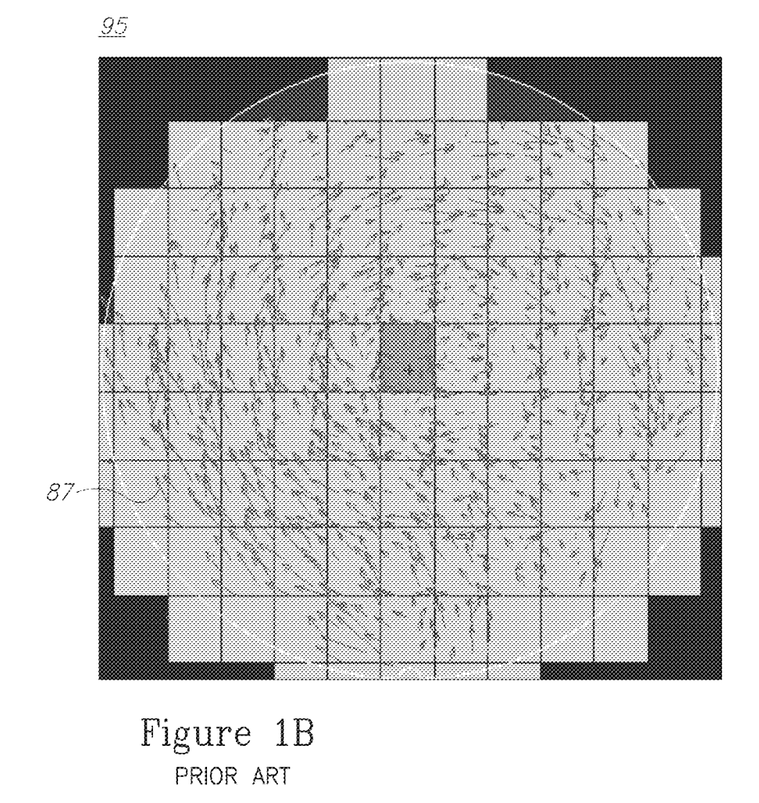
FIG. 1B illustrates a rotation term effect resulting from the prior art practice of leaving empty background regions between target elements.

FIGS. 1A and 1B illustrate a dishing effect and a rotation term effect, respectively, as resulting from the prior art practice of leaving empty background regions between target elements. FIG. 1A schematically illustrates prior art target 90, comprising segmented target elements 90A separated by empty background regions 90B. Typical and non-limiting dimensions for the illustrated target parts are on the scale of micrometers, e.g., the widths of target element 904 and of empty background regions 90B may be within a range of 0.5-1 μm (in their shorter dimension) and the respective target pitch may be within a range of 1-2 μm. The graphical representations shown in FIG. 1A are of a "dishing effect" that results from empty background regions 90B, namely uneven or non-planar layer regions 85 which form above empty background regions 90B due to characteristics of process steps such as etching, deposition or polishing. In the illustrated example, simulation results for deposited layers 83 are presented (approximate scales of layer height h versus displacement y are given), showing significant accuracy issues, depending on the dishing depth (top right—no dishing, middle right—5 nm dishing, bottom right—15 nm dishing). The overlay (OVL) values represent only this OVL inaccuracy, since the induced OVL value in the simulation was zero. The deeper the dishing, the more significant is the measured inaccuracy OVL.

Another effect, illustrated in FIG. 1B, results in a large scale, global effect of such uneven layer regions 85. For example, during the Chemical Mechanical Polishing/Planarization (CMP) process, empty regions 90B between target features 904 may become somewhat concave and introduce asymmetric polishing of target elements 904 which border these empty regions 90B. The asymmetric polishing results in measurement errors that are at least partly quantified by a "rotation term" of inaccuracy, which reflects a cumulative effect of asymmetric polishing of target elements 90A bordering empty regions 90B, relating to the rotational movement of the polish pad. FIG. 1B illustrates experimental results that illustrate the rotation term that originates from asymmetric polishing of empty regions in target 90. In the illustrated case, targets 90 are Box-in-Box targets (left of FIG. 1B) which have a central empty region (as well as peripheral empty regions) in which the dishing effect occurs. Image 95 is an overview of a wafer, in which the overlays relating to individual targets 90 are marked by arrows 87. The rotation term is evident in the overall circular pattern of overlays 87, having larger overlays 87 with increasing distance of targets 90 from the center of the wafer. The rotation term originates from asymmetric polishing of empty regions 90B in targets 90. In the example illustrated in FIG. 19, the rotation term (measured as a ratio between the rotational overlay and the distance from the center of the wafer) is ca. 0.02 ppm.

Commonly used imaging and scatterometry metrology targets such as BiB, AIM, AIMid, SCOL or DBO may have relatively large empty regions 90B without any pattern which provide contrast for optical measurements. These empty regions are typically 4-20 μm long and 300 nm-2 μm wide. Such dimensions commonly cause the dishing effect and resulting rotation term illustrated above.

Thus, there is a long felt need for a target design with improved robustness for the CMP (Chemical Mechanical Polish) process.

SUMMARY OF THE INVENTION

One aspect of the present invention provides a metrology target comprising specified filling elements introduced into identified continuous regions in a given target design, wherein parameters of the introduced filling elements are determined by a trade-off between a contrast requirement and an inaccuracy requirement which is associated via production with the identified continuous regions.

The present invention also provides a method of designing metrology targets having the steps of identifying continuous regions in a target design, and introducing specified filling elements into the identified continuous regions, wherein parameters of the introduced filling elements are determined by a trade-off between a contrast requirement and an inaccuracy requirement which is associated via production with the identifying continuous regions. At least one of the identifying and the introducing can be carried out by at least one computer processor.

The present invention also provides metrology measurement equipment configured to measure a metrology target produced by the method comprising the steps of identifying continuous regions in a target design, and introducing specified filling elements into the identified continuous regions, wherein parameters of the introduced filling elements are determined by a trade-off between a contrast requirement and an inaccuracy requirement which is associated via production with the identifying continuous regions, and wherein at least one of the identifying and the introducing is carried out by at least one computer processor.

The present invention also provides a computer-based apparatus comprising a memory element configured to store a plurality of computer-readable instructions, and a processor configured to execute the plurality of computer-readable instructions to identify continuous regions in a target design and introduce specified filling elements into the identified continuous regions, wherein parameters of the introduced filling elements are determined by a trade-off between a contrast requirement and an inaccuracy requirement which is associated via production with the identifying continuous regions.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION

Prior to the detailed description being set forth, it may be helpful to set forth definitions of certain terms that will be used hereinafter.

The terms "metrology target" or "target", as used in this application, are defined as any structure designed or produced on a wafer which is used for metrological purposes. Non-limiting examples for metrology targets are imaging targets such as Box-in-Box (BiB) targets and scatterometry targets such as periodic structures (e.g., gratings). The terms "metrology target" or "target" as used in this application may refer to any other target design, e.g., AIM (advance image metrology), variants thereof and alternatives therefor, AIMid, Blossom targets, variants thereof and alternatives therefor, SCOL (scatterometry overlay) targets and alternatives therefor, DBO (diffraction based overlay) target and variants thereof, etc. The terms "metrology target" or "target" as used in this application may refer to one or two dimensional targets, or to one or two dimensional target elements. A target is referred to as comprising target elements, each "target element" being a feature of the target that is to be distinguished from its background, the "background" being a wafer area proximate to a target element on the same or on a different layer (above or below the target element).

The term "target element", as used in this application, is defined as a feature in the metrology target such as individual target areas or boxes, grating bars etc. Target elements may segmented, i.e., may comprise multiple smaller features. Each "target element" is a feature of the target that is to be distinguished from the target background.

The term "target part", as used in this application, is used to refer to a part of a target that is illustrated in the figures, and does not limit the scope of disclosed target design principles.

The term "periodic structure", as used in this application, refers to any kind of designed or produced structure in at least one layer which exhibits some periodicity. The periodicity is characterized by its pitch, namely its spatial frequency. For example, a bar as a target element may be produced as a group of spaced parallel lines, thereby reducing the minimal feature size of the element and avoiding monotonous regions in the target.

The terms "previous layer" and "current layer", as used in this application, refer to any two layers of a metrology target which are produced sequentially, the current layer upon the previous layer. For example, a previous layer may be an oxide layer and a current layer a poly-silicon layer, or vice versa. A previous layer may comprise outer target elements and a current layer may comprise inner target elements, or vice versa.

The terms "continuous region", "empty region" or "full bar", as used in this application, are defined as continuous target elements having dimensions which are large with respect to typical device features and hence involve production inaccuracies as described below. While most of the description refers to empty regions as the continuous regions in target designs, it is explicitly noted that similar design principles are applicable to full bars as continuous regions and respective targets are likewise part of the disclosed invention.

The terms "filling element" or "gap element", as used in this application, are defined as elements which are smaller than the empty region and the full bar, respectively, and are used to break down the continuity of the empty region and the full bar, respectively, as explained and illustrated in detail below. Specifically, the term "filling elements" is used to refer to any continuous regions, i.e., both to elements filling empty regions as well as to filling elements as gaps in full bars. While most of the description refers to filling elements in empty regions, it is explicitly noted that similar design principles are applicable to gap elements filling fill bars and respectively designed targets are likewise part of the disclosed invention.

The terms "metrology measurement" or "measurement" as used herein in this application, are defined as any metrology measurement procedure used to extract information from metrology targets. For example, metrology measurements may be imaging of the targets or scatterometry measurements of the targets. Non-limiting examples for metrology measurements include overlay measurement (imaging or scatterometry), critical dimension (CI)) measurement, focus and dose measurement, etc.

The term "scatterometry overlay (SCOL)", as used in this application, refers to a metrology method that derives metrology information from the phases of diffraction orders (e.g., the +1 and −1 diffraction orders) that reflect off targets which contain periodic structures such as gratings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The invention is aimed at improving the process robustness of overlay targets and other optical targets. It is done by chopping the open spaces (empty regions 90B) with small features (filling elements 110), improving the robustness for CMP (Chemical Mechanical Polish) process but without changing the measurement methods and algorithms. This is done through minimal impact to the contrast so no changes to hardware or algorithm are needed.

Target designs 100 disclosed herein comprise segmented target elements 90A and background regions 90B. Background regions 90B are not left empty, but comprise filling elements 110 to prevent the CM process from polishing segmented target elements 90A asymmetrically or at least reduce the degree of asymmetrical polishing. Similar designs may be used to reduce or eliminated other inaccuracies that originate from biases introduced in production steps by relatively large empty spaces, for example ones that originate from etching or deposition steps. Filling elements 110 may be introduced into empty spaces in different and/or multiple layers, with appropriately adjusted parameters.

Metrology targets 100 comprise specified filling elements 110 introduced into identified empty regions 90B in a given target design (e.g., regions 90B having a width of at least 300 nm and lacking features within regions 90B), wherein parameters of introduced filling elements 110 are determined by a trade-off between a contrast requirement, and an inaccuracy requirement which is associated via production with identified empty regions 90B. Either or both the contrast requirement and the inaccuracy requirement may comprise multiple requirements, relating to different aspects of contrast and/or inaccuracy, as well as possibly relating to other aspects of the target production and metrology measurements. The trade-off may involve any of the respective parameters and may be defined according to given specifications, concerning either or both production and measurements. The trade-off may be determined theoretically or experimentally, and may involve feedback received in a training or experimental phase. The trade-off may be adjusted according to results of simulations and/or of actual metrology measurements.

For example, in metrology targets 100 having at least one segmented target element 90A and at least one background area of at least one segmented target element 90A, specified filling elements 110 may be introduced into identified empty regions 90B in the at least one background area, and the contrast requirement may relate to target element 90A contrast to its background area, i.e., filling elements 110 are selected to maintain the contrast using regular optical measurements. In certain embodiments, however, the optical measurements may be adapted to distinguish filling elements 110 from target elements 90A, using various techniques (e.g., measuring light polarization). Metrology targets 100 may be configured to yield, when used at a wafer level, a rotation term below a specified threshold, e.g., significantly below 0.02 ppm.

In certain embodiments, specified filling elements 110 may comprise at least one first periodic structure having first specified parameters and target elements 90A may comprise at least one second periodic structure having second specified parameters. The first specified parameters may be selected to differ from the second specified parameters to an extent that satisfied the contrast requirement and enables metrology measurements to distinguish target elements 90A from background regions 90B having filling elements 110. The difference between the first and second specified parameters, with respect to the respective periodic structures, may comprise any of the following parameters: the pitch of the first and second periodic structures, the orientation thereof, the pattern thereof, dimensions of segments in the first and second periodic structures, an aspect ratio of the segments and the topography of the first and second periodic structures. Any of these may be selected to maintain the required contrast above a specified threshold.

Targets 100 may be configured to be compatible with specified design rules.

Figure 2A:
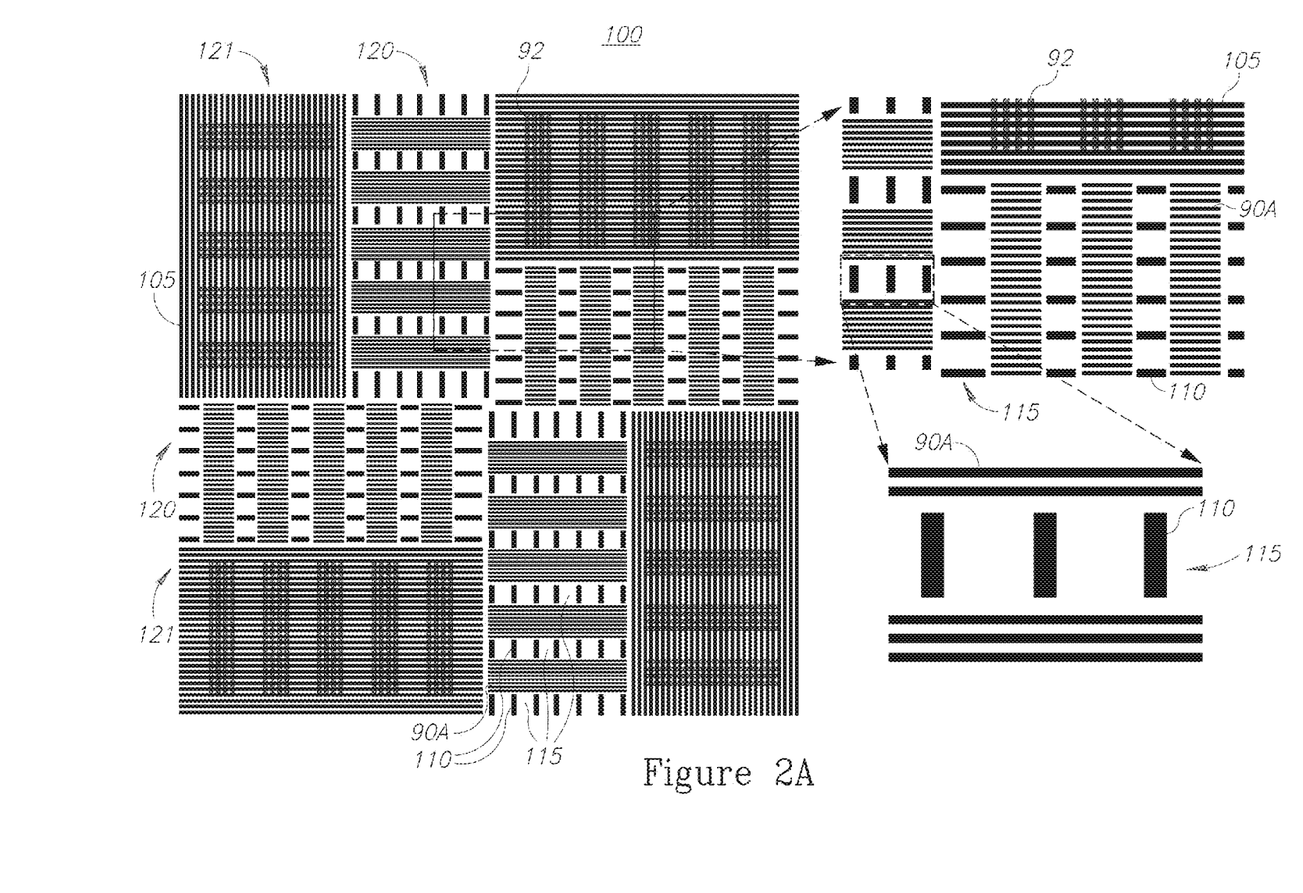
FIG. 2A is a high level schematic illustration of metrology targets with filling elements introduced into identified empty background regions, according to some embodiments of the invention.

FIG. 2A is a high level schematic illustration of metrology target 100 with filling elements 110 introduced into identified empty background regions 115, according to some embodiments of the invention. Background regions 115 represent empty background regions 90B which were identified and redesigned to include filling elements 110. FIG. 2A illustrates AIM target 100 comprising target elements 90A in a current, inner, layer 120 (e.g., an oxide layer) and target elements 92 in a previous, outer, layer 121 (e.g., a poly-silicon layer). In the illustration, target elements 90A as well as target elements 92 are segmented, as is background. 105 of previous layer 121.

Filling elements 110 are introduced into background regions 115 which were left empty in prior art targets 90 (compare e.g., to FIG. 1A). Filling elements 110 are configured to reduce the unwanted polishing bias while not reducing significantly the contrast between target elements 90A and their background 115. For example, the density and dimensions of filling elements 110 may be selected to prevent the dishing effect but still fill a relatively small part of empty regions 90B, and hence reduce contrast only to a small extent. Filling elements 110 may be introduced in densities and/or patterns which preserve the optical contrast between target elements 904 and their respective background regions 115, to allow using unmodified measurement equipment.

It is noted that background regions 115 are preferably not filled with segmented patterns of similar density to target element segmentation, because then differentiating target elements 90A from background regions 115 during measurements may require respective adaptation of the measurement equipment, for example using a polarizer to differentiate between regions (e.g., 90A, 115) which are segmented in different directions. However, certain embodiments may comprise adaptation of the optical measurement methods and equipment. Filling elements 110 may be introduced in various patterns and orientations, according to production and measurement considerations.

For example, the density of filling elements 110 in background regions 115 may be half to one tenth of the density of target element 90A segmentation. In certain embodiments, the density ratio between filling elements 110 in background regions 115 and target element 904 may be between 1:4 to 1:100 or more. A low density of filling elements 110 reduces the loss of accuracy due to the fact that regions 115 are not as empty as regions 90B. In certain embodiments, the density ratio between filling elements 110 in background regions 115 and the target element 90A segmentation may be 1:4 to 1:6, as illustrated in a non-limiting manner in FIG. 2A, in which the density ratio is about 1:8 in terms of spatial frequency and about 1:4 in terms of total width (filling elements 110 fill about a fourth of the area of background regions 115; each filling element 110 is about twice as wide as a segment in target element 904). The inventors have found that introducing filling elements 110 has eliminated a rotation term of 0.02 ppm (millionths of radians) in the case illustrated in FIG. 1B. The density of filling elements 110 may be adjusted according to contrast requirements for targets 100 and according to the measurement equipment that is being used.

Figure 2B:
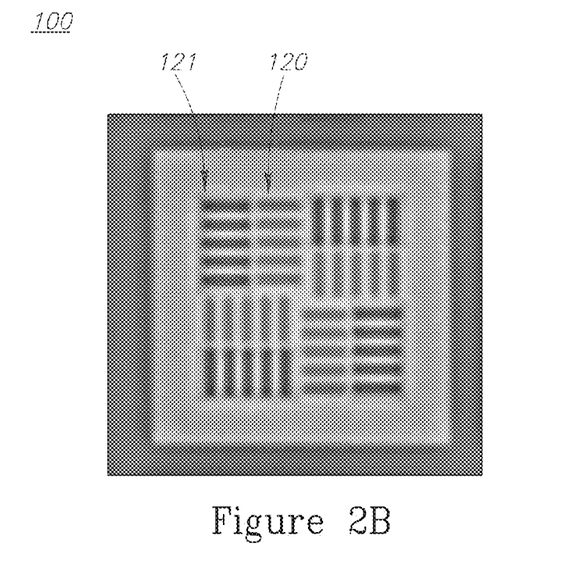
FIG. 2B is an illustrative example of an image of an AIM (advance image metrology) target as illustrated in FIG. 2A, according to some embodiments of the invention.

FIG. 2B is an illustrative example of an image of AIM target 100 as illustrated in FIG. 2A, according to some embodiments of the invention. Target image 100 exhibits two levels of contrast for current layer 120 and previous layer 121, respectively, namely a high contrast between target elements 92 and their background 105 in the outer elements and a medium contrast between target elements 904 and their background 115 in the inner elements. White adding filling elements 110 into background regions 115 reduces their contrast with respect to adjacent target elements 90A, controlling the density of filling elements 110 (and generally their sizes and parameters such as width, length, height, orientation, pattern and other parameters) allows keeping the loss of contrast acceptable, or even avoiding any loss of contrast.

Figure 2C:
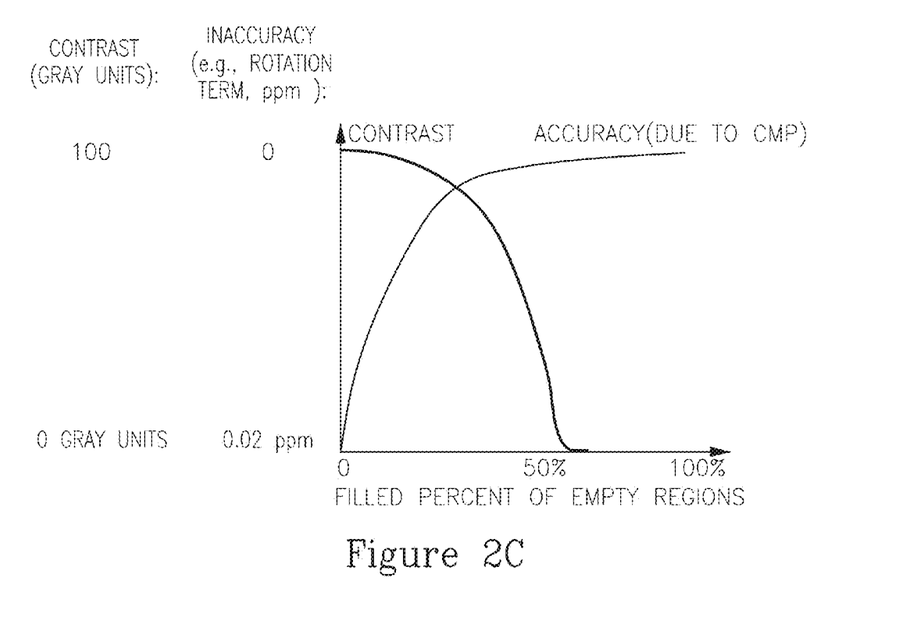
FIG. 2C is a high level schematic example for the trade-off between the contrast and the inaccuracy requirements, according to some embodiments of the invention.

FIG. 2C is a high level schematic and illustrative example for the trade-off between the contrast and the inaccuracy requirements (with respect to the inaccuracy that is associated via production with identified empty regions, referred to in FIG. 2C in a non-limiting manner as a CMP inaccuracy). FIG. 2C represents a semi-quantitative expression of phenomena which were identified by the inventors and utilized for the purpose of the present invention. FIG. 2C depicts, in a non-limiting manner, the decrease in contrast as filling elements 110 are added to fill an increasing percentage of empty regions 90B. In the illustrated example, the contrast is measured as gray units ranging from 0 (no contrast) to 100 (maximal contrast). FIG. 2B provides a visual impression of a high contrast level in regions 121 and an intermediate contrast level in regions 120. It is noted that a low filling level of the empty regions results in a mild reduction in contrast, while a filling percentage of ca. 50% reduces the contrast to practically zero. FIG. 2C also depicts the increase in accuracy (due to process aspects as described above) as filling elements 110 are added to fill an increasing percentage of empty regions 90B. The inaccuracy is expressed as the rotation term in a non-limiting manner, and may expressed by any other parameter if needed, with respect to the relevant production processes. In contrast to the way contrast decreases, the larger part of accuracy increase is achieved already by introducing filling elements 110 in a relatively small part of the empty regions. For example, at a filling percentage of 25% (1:4) in the illustrated graph, the inaccuracy is reduced almost to zero while the contrast is reduced only in a small measure. Determination of the specific filling percentage, as well as of other characteristics and parameters of filling elements 110, may hence be determined according to the accuracy-contrast trade-offs expressed in respective graphs that are simulated, calculated or measured for specific use cases.

Figure 2D:
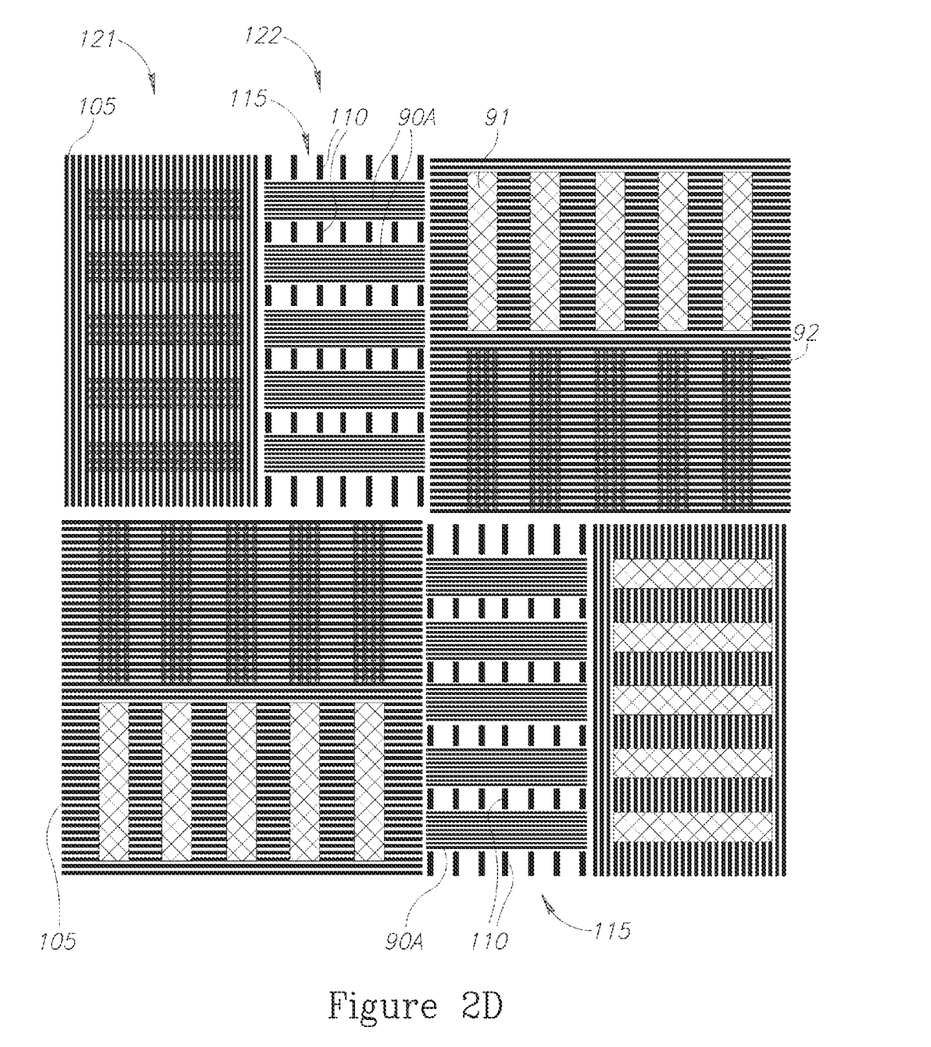
FIG. 2D is a high level schematic illustration of metrology targets with filling elements introduced into identified empty background regions, according to some embodiments of the invention.

FIG. 2D is a high level schematic illustration of metrology target 100 with filling elements 110 introduced into identified empty background regions 115, according to some embodiments of the invention. In FIG. 2D additional target elements 91 are part of the target, e.g., as an uppermost layer (e.g., contact layer) or as any other layer. Target elements 91 may be segmented or not, and may have segmented background 105 as their background. Target 100 is hence a three layer target with alignment to one layer in one direction and to another layer in another direction, and is an example of a more general use case of multilayer targets. Background regions in any part and in any layer of any type of target may be occupied by filling elements 110. Moreover, the type, the orientation, the pattern or the density of filling elements 110 may vary between different parts or layers of target 100.

Figure 2E:
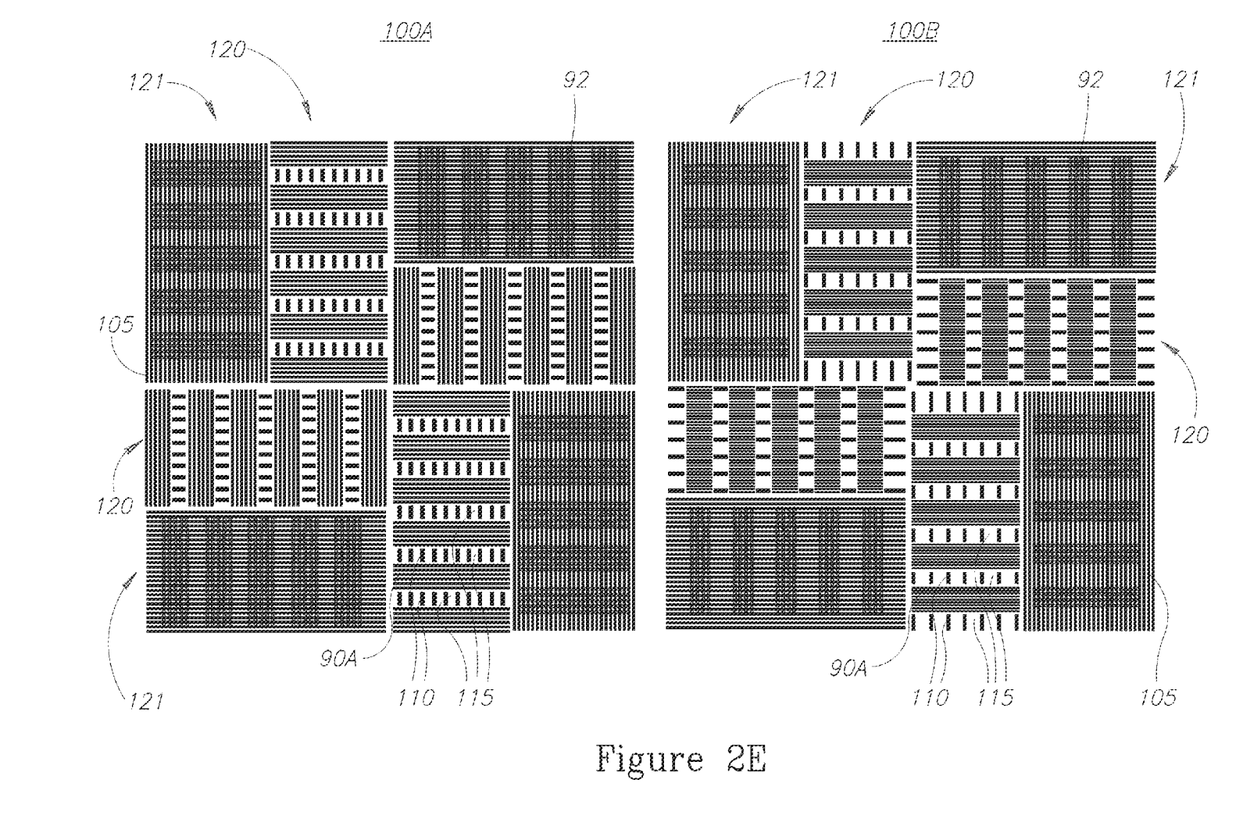
FIG. 2E is an exemplary schematic illustration of targets having different target element segmentation and varying densities and frequencies of filling elements, according to some embodiments of the invention.

FIG. 2E is an exemplary schematic illustration of targets 100A, 100B having different target element segmentation and varying densities and frequencies of filling elements 110, according to some embodiments of the invention. Target elements 90A, 92 in different targets and in different target layers may be segmented differently, and their contrast requirements with respect to their adjacent background regions 115, 105 (respectively) may differ among locations on the targets and among layers. The characteristics of filling elements 110 may be designed to comply with any of the contrast requirements per specific situation (e.g., target, layer, measurement conditions etc.).

Figure 3A:
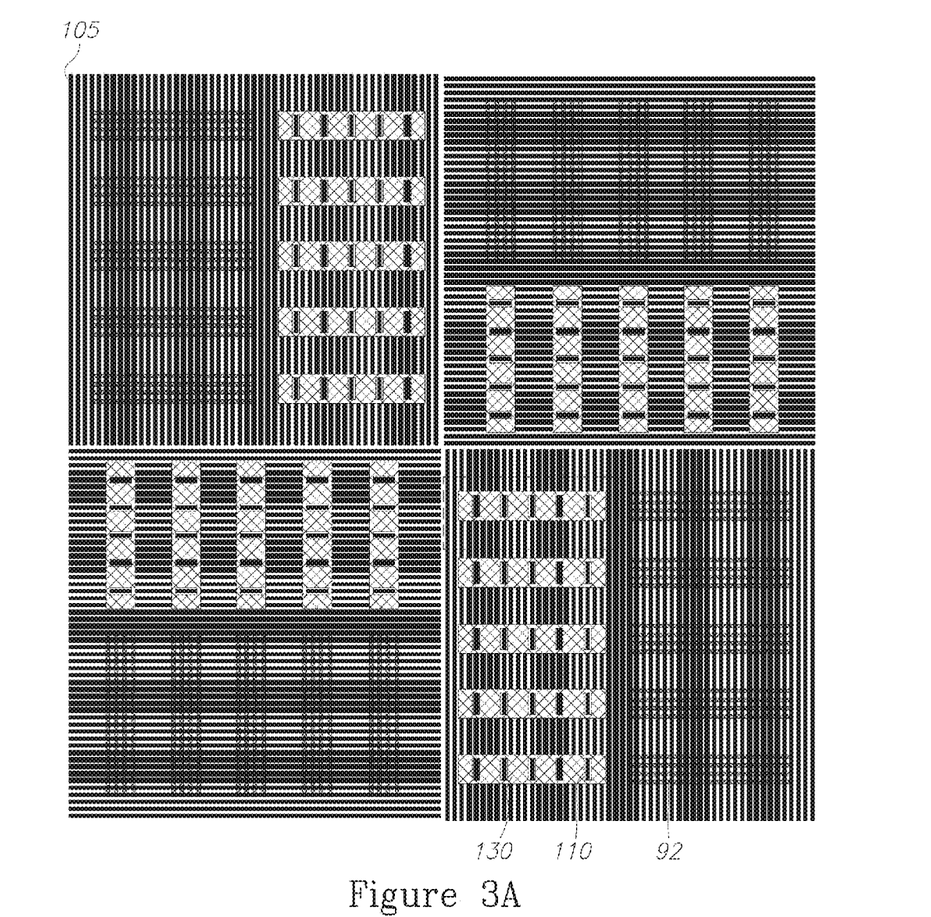
FIG. 3A is an exemplary schematic illustration of a target and of a production method of filling elements, according to some embodiments of the invention.
Figure 3B:
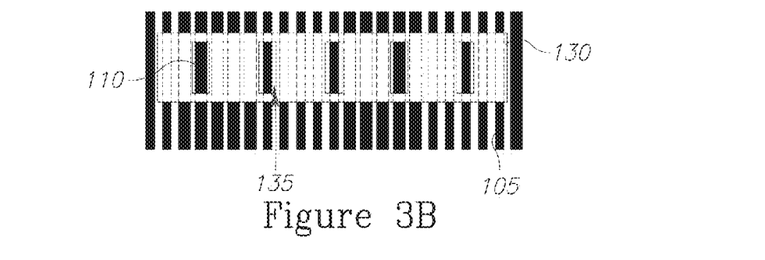
FIG. 3B is an exemplary schematic illustration of a target and of a production method of filling elements, according to some embodiments of the invention; and, FIG. 4 is a high level schematic flowchart illustrating a method, according to some embodiments of the invention.

FIGS. 3A and 3B are exemplary schematic illustrations of target 100 and of a production method of filling elements 110, according to some embodiments of the invention. Filling elements 110 may be produced by a cutting mask 130 (FIG. 3B) and a cutting process applied, for example to segmented background region 105 or to a part of it. For example, as illustrated in FIG. 3A, an empty or blank region of target 100 may be segmented, e.g., in a similar manner to target elements 90A, 92 or to segmented background regions 105, and then segments and segments' parts may be removed to leave behind only filling elements 110 in specified sizes, patterns and density. Spaces 135 in cutting mask may be designed to produce specified filling elements 110. Background segmentation 105 may be designed and produced to have a varying spatial frequency, pitch and/or segment width, and filling elements 110 may also vary in their parameters.

In certain embodiments, empty regions 90B may be full bars and filling elements 110 may be gaps 110 within full bars 90B. Such filling gaps 110 may enhance the accuracy of production of full bars 90B and prevent inaccuracies such as may be introduced during the production processes. The respective metrology targets may be designed in a similar way, by identifying full bars 90B in the target design and introducing specified filling gap elements 110 into identified full bars 90B. The parameters of the introduced gap elements 110 may be determined by similar trade-offs between contrast requirements and inaccuracy requirements, the latter being associated via production with the identifying full bars 90B.

The disclosed design may be applied to any type of target that include empty background regions, such as Box-in-Box targets, AIM targets and AIMid targets.

The inventors have found experimentally that the disclosed targets and methods are more efficient and provide increased accuracy with respect to prior art targets and methods.

Certain embodiments of the disclosed invention comprise metrology measurement equipment, configured to measure any of the disclosed metrology targets as well as production equipment, configured to produce any of the disclosed metrology targets.

Figure 4:
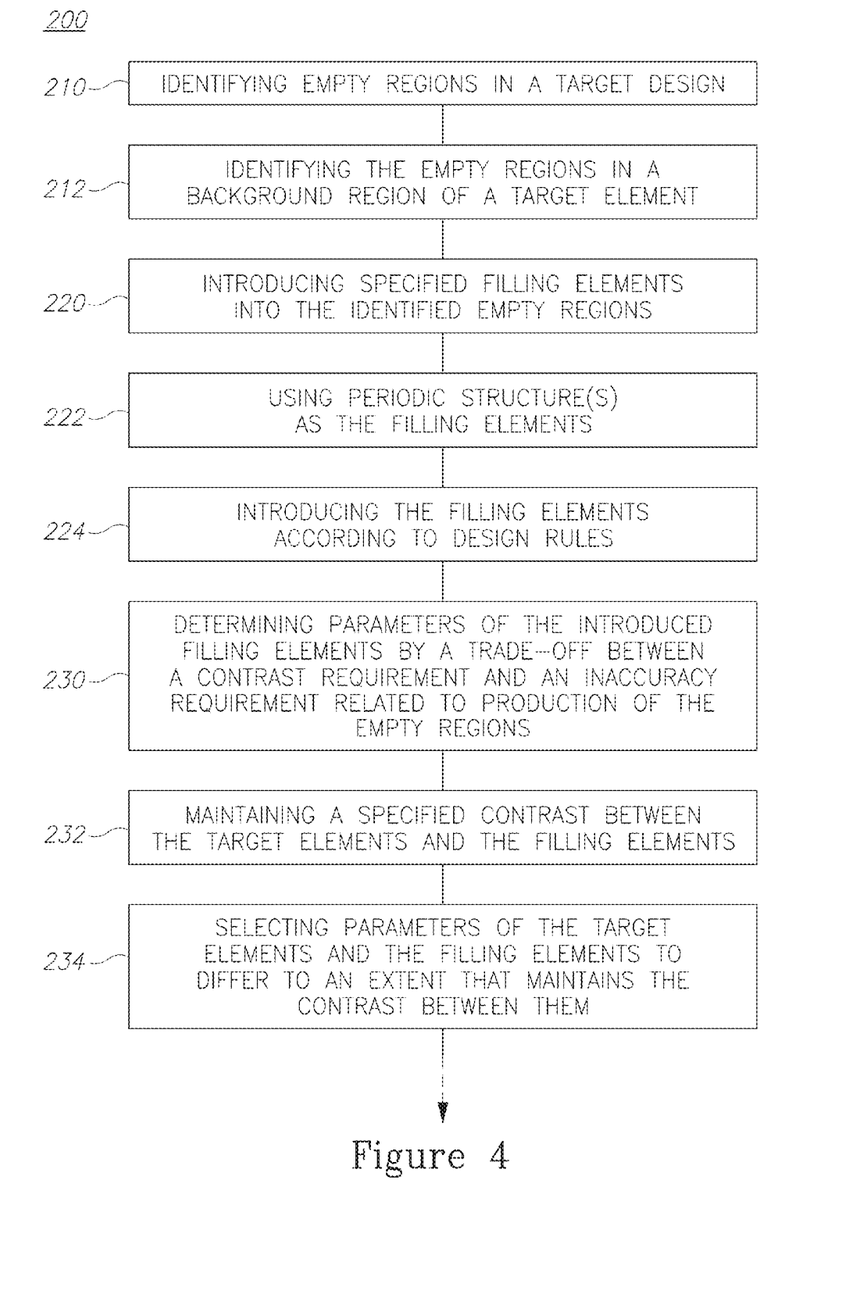

FIG. 4 is a high level schematic flowchart illustrating a method 200, according to some embodiments of the invention. Method 200 comprises designing metrology targets and designing and/or producing target design files and targets (stage 240) using any of the following stages.

Method 200 comprises identifying empty regions in a target design (stage 210) and introducing specified filling elements into the identified empty regions (stage 220). Parameters of the introduced filling elements may be determined (stage 230) by a trade-off between a contrast requirement and an inaccuracy requirement which is associated via production with the identifying empty regions. At least one of identifying 210 and introducing 220 is carried out by at least one computer processor.

Identifying the empty regions 210 may be carried out in at least a background area of a target element (stage 212) and the contrast requirement may be related to target element contrast to its bkkground area, which may be maintained above a specified threshold (stage 232).

The inaccuracy requirement may be set to be a rotation term (stage 238, see e FIG. 1B).

Periodic structure(s) may be used as at least parts of the specified filling elements (stage 222). First periodic structure (s) of the specified filling elements may have first specified parameters, while the target elements may comprise at least one second periodic structure having second specified parameters. The first specified parameters may be selected to differ from the second specified parameters to an extent that satisfied the contrast requirement (stage 234) and maintain the contrast between the target elements and the background with the filling elements above a specified threshold. For example, method 200 may comprise selecting periodic structures of the target elements and the filling elements to differ in at least one of their pitch, orientation, pattern, segment dimensions, aspect ratio and/or topography (stage 236). Any of the pitch of the first and second periodic structures, the orientation thereof, the pattern thereof, dimensions of segments in the first and second periodic structures, an aspect ratio of the segments and the topography of the first and second periodic structures may be selected to maintain the required contrast above a specified threshold.

Introducing of the specified filling elements 220 may be carried out according to specified design rules (stage 224) to produce design-wle-compatible targets. Producing the filling elements may be carried out using a cutting mask (stage 226), e.g., applied upon a segmented region.

Method 200 may further comprise carrying out any of the stages by at least one computer processor (stage 242), and further disclosed are target design files and metrology targets designed and/or produced according to any of the stages of method 200. Further disclosed are computer program products comprising computer readable storage media having computer readable program embodied therewith, the computer readable program configured to carry out any of the stages of method 200.

Advantageously, the disclosed targets and methods exhibit polish and/or etch process robustness, reduce inaccuracy and eliminate the inaccurate rotation term, possibly while using the same measurement and computation techniques (metrology optical tools, methods and measurement algorithms).

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method of designing metrology targets comprising:
identifying, with one or more processors, one or more continuous regions in a target design;
introducing, with the one or more processors, one or more selected filling elements into the one or more identified continuous regions to form a modified target design, wherein one or more parameters of the one or more introduced filling elements are determined based on a contrast requirement and an inaccuracy requirement of the modified target design, wherein contrast and inaccuracy are dependent on an amount of empty region within the one or more continuous regions; and producing a target with the modified target design on a wafer.

2. The method of claim 1, wherein the step of identifying is carried out in at least a background area of a target element.

3. The method of claim 1, wherein the inaccuracy requirement is a rotation term.

4. The method of claim 1, wherein the selected one or more filling elements comprise at least one periodic structure.

5. The method of claim 1, wherein the selected one or more filling elements comprise at least one first periodic structure having a first set of selected parameters, and target elements comprising at least one second periodic structure having a second set of selected parameters, wherein the first set of selected parameters differ from the second set of selected parameters by an extent necessary to satisfy the contrast requirement.

6. The method of claim 5, wherein at least one of the first set of selected parameters or the second set of selected parameters comprise at least one of a pitch, an orientation, a pattern, a dimension of one or more segments, an aspect ratio or a topography.

7. The method of claim 1, wherein the step of introducing is carried out according to a selected set of design rules.

8. The method of claim 1, further comprising producing one or more metrology targets including the one or more filling elements.

9. The method of claim 8, wherein the one or more filling elements are formed with a cutting mask.

10. A metrology system comprising:
a metrology tool configured to measure overlay from one or more metrology targets, wherein the one or more metrology targets comprise:
one or more selected filling elements positioned within one or more identified continuous regions of the metrology target, wherein one or more parameters of the one or more introduced filling elements are based on a contrast requirement and an inaccuracy requirement of the metrology target, wherein contrast and inaccuracy are dependent on an amount of empty region within the one or more identified continuous regions.

11. A metrology target comprising:
one or more selected filling elements positioned within one or more identified continuous regions of the metrology target, wherein one or more parameters of the one or more introduced filling elements are based on a contrast requirement and an inaccuracy requirement of the metrology target, wherein contrast and inaccuracy are dependent on an amount of empty region within the one or more identified continuous regions.

12. The metrology target of claim 11, further comprising:
at least one segmented target element,
wherein the segmented target element includes at least one background area,
wherein the one or more selected filling elements are introduced into the one or more identified continuous regions in the at least one background area, and
wherein the contrast requirement comprises a contrast requirement of the segmented target element relative to the at least one background area.

13. The metrology target of claim 11, wherein the selected one or more filling elements comprise at least one first periodic structure having a first set of selected parameters, and one or more target elements comprising at least one second periodic structure having a second set of selected parameters, wherein the first set of selected parameters differ from the second set of selected parameters by an extent necessary to satisfy the contrast requirement.

14. The metrology target of claim 13, wherein the one or more target elements are segmented and wherein a density of the one or more filling elements in the one or more identified continuous regions is between half and one tenth of a density of the segmentation of the one or more target elements.

15. The metrology target of claim 13, wherein at least one of the first set of selected parameters or the second set of selected parameters comprise at least one of a pitch, an orientation, a pattern, a dimension of one or more segments, an aspect ratio or a topography.

16. The metrology target of claim 11, configured to yield a rotation term below a selected threshold.

17. The metrology target of claim 11, wherein the selected one or more filling elements comprise at least one periodic structure.

18. The metrology target of claim 11, wherein one or more structures of the metrology target are compatible with a selected set of design rules.

19. The metrology target of claim 11, wherein the one or more identified continuous regions are at least 300 nm in width.

20. A metrology system comprising:
a metrology tool configured to measure overlay from one or more metrology targets, wherein the one or more metrology targets comprise:
one or more segmented target elements including one or more background regions; and
one or more selected filling elements positioned within one or more identified continuous regions within the one or more background regions, wherein one or more parameters of the one or more introduced filling elements are based on a contrast requirement and an inaccuracy requirement of the metrology target, wherein contrast and inaccuracy are dependent on an amount of empty region within the one or more identified continuous regions.

21. An apparatus comprising:
a memory element configured to store a plurality of computer-readable instructions; and
a processor configured to execute the plurality of computer-readable instructions to:
identify one or more continuous regions in a target design;
introduce one or more selected filling elements into the one or more identified continuous regions to form a modified target design, wherein one or more parameters of the one or more introduced filling elements are determined based on a contrast requirement and an inaccuracy requirement of the modified target design, wherein contrast and inaccuracy are dependent on an amount of empty region within the one or more continuous regions; and
direct a production tool to produce a target with the modified target design on a wafer.

22. The apparatus of claim 21, wherein the processor is configured to execute the plurality of computer readable instructions to produce the one or more selected filling elements using a cutting mask.

* * * * *